United States Patent
O'Neill

[11] Patent Number: 4,745,807
[45] Date of Patent: May 24, 1988

[54] DENSITY METER FOR CONTINUOUS FLUID FLOW

[76] Inventor: Timothy P. O'Neill, 417 Poppy Pl., Mountain View, Calif. 94043

[21] Appl. No.: 927,497

[22] Filed: Nov. 6, 1986

[51] Int. Cl.⁴ .............................................. G01N 9/06
[52] U.S. Cl. ...................................................... 73/434
[58] Field of Search ................. 73/433, 434, 435, 436, 73/437

[56] References Cited

U.S. PATENT DOCUMENTS

| | | |
|---|---|---|
| 1,033,398 | 7/1912 | Heylandt . |
| 1,522,886 | 1/1925 | Heylandt . |
| 2,321,175 | 6/1943 | Binckley ............................. 73/434 |
| 2,762,761 | 9/1956 | Stanley et al. . |
| 2,991,900 | 7/1961 | Poorman . |
| 3,039,310 | 6/1962 | Copland et al. ....................... 73/434 |
| 3,812,723 | 5/1974 | Barron . |
| 4,285,239 | 8/1981 | Heine et al. . |
| 4,372,405 | 2/1983 | Stuart .................................. 73/437 |

Primary Examiner—John Chapman
Attorney, Agent, or Firm—William W. Haefliger

[57] ABSTRACT

A density meter for continuous fluid flow including a plurality of hollow flexures, a relatively fixed support for one end for each of the flexures, and a closed container supported by, and interiorly communicating with, the opposite ends of the flexures. One or more of the flexures conduct a flowing fluid into the container, and the other of the flexures conduct a flowing fluid out of the container. Changes in fluid density produce flexure deflection, the container when filled with fluid being supported in every position by the deflecting flexures. A transducer is provided to convert such deflection into an electrical displacement signal, and a first processor is connected to the transducer to convert such electrical displacement signal to an electrical weight signal. An additional element is provided to produce an electrical volume signal, and a second processor is connected to the first processor and to the additional element to combine the weight signal with the volume signal to produce a density signal, which may be temperature and pressure compensated.

7 Claims, 6 Drawing Sheets

DENSITY METER FOR CONTINUOUS FLUID FLOW

BACKGROUND OF THE INVENTION

This invention generally relates to improvements in continuous flow density meters.

The standard method for precisely determining the density of fluids involves the use of a closed pressure vessel, commonly known as a pycnometer, whose volume is precisely determined, and of an accurate weighing device. The weighing device is calibrated using standard weights traceable to the National Bureau of Standards (NBS). The pycnometer consists of a valved bulb of known volume that is filled with the sample, valve closed and weighed on the weighing device. The volume of the pycnometer bulb is corrected for the temperature and pressure of the sample; that is, as the temperature and pressure increase, the walls of the bulb expand, causing an increase in volume that must be considered for accurate density calculations. The volume calibration of the pycnometer is generally described in a bulletin published by the American Petroleum Institute; API MPMS Chapter 11.2.3- "Water Calibration of Volumetric Provers." This method is related to the volume calibration method described below for the continuous density meter described herein.

The direct weigh method is accepted as a batch method for determining density, but until the present invention has not been practical for continuous monitoring of density. A major problem has been that when the pycnometer is connected to a source for continuous flow, the flow connections interfere with the accuracy of the weighing device. The flow connections must be able to withstand high pressures, extremes of temperatures, and be of a large enough diameter to accomodate a high flow in order to continuously change the sample in the bulb. The bulb must be of large enough size that small change in density may be resolved. Flexible connections either do not tolerate these hostile conditions or they produce twisting forces that interfere with accurate weighing. Rigid connections do not allow free movement of the bulb or develop resonant vibrations that cause oscillating feedback in the weighing device.

SUMMARY OF THE INVENTION

An object of this invention is to provide means for producing signal that is proportional to the weight of a continuously flowing sample of fluid.

A further object of this invention is to provide means by which a continuously flowing sample, the weight of which is to be accurately determined, may be passed through the instrument at the same pressure as the source.

Another object of this invention is to provide means by which a continuously flowing sample, the weight of which is to be accurately determined, may be passed through the instrument at the same temperature as the source.

Another object of this invention is to provide means for producing a signal that is proportional to the volume of a continuously flowing sample of fluid within a range of temperature and pressure combinations.

Another object of this invention is to provide means for processing the first signal that is proportional to the instantaneous weight of a sample and the second signal that is proportional to the instananeous volume of said sample, in order to produce a third signal that is proportional to the instantaneous density of said sample.

Another object of the invention is to provide means for determining the density of a continuously flowing fluid that is calibrated directly with weight standards traceable to the National Bureau of Standards.

Other objects of the invention will appear as the description thereof proceeds.

In the present invention the connection problem is solved by using the connections as the weighing device; that is, the main flexures of the weighing device are hollow and serve the dual purpose of flexures and flow connections. In this regard, U.S. Pat. No. 2,231,175 describes a mechanical device that uses "spring tubes" to partially support the bulb. In the present invention the spring tube concept is refined and improved; and it is combined with devices for electronically determining displacement of the flexures, temperatures and pressure and with microprocessor based signal processing. The end result is a continuous density meter that is highly accurate and reliable, while remaining based on a simple, straight-forward principle of operation.

The invention provides a continuous density meter system which is mechanically simple in construction, relatively inexpensive in cost of manufacture and assembly, and generally superior to continuous density meters now known to applicant in that it is based on the straight-forward concept of determining the weight and the volume of the sample, and of calculating density by simple arithmetic division. It is the only continuous density meter that utilizes the direct weight technique, to my knowledge.

A further object comprises the novel and useful provision, formation, construction, association and relative arrangements of parts, members, and features, all as depicted in a certain embodiment in the accompanying drawings, described generally, and more particularly pointed out in the claims.

DRAWING DESCRIPTION

The disclosure of the invention described herein represents the preferred embodiments of the invention; however, variations thereof, in the form, construction, and arrangement of the various components thereof and the modified application of the invention are possible without departing from the spirit and scope of the claims.

DETAILED DESCRIPTION

Figure 1:
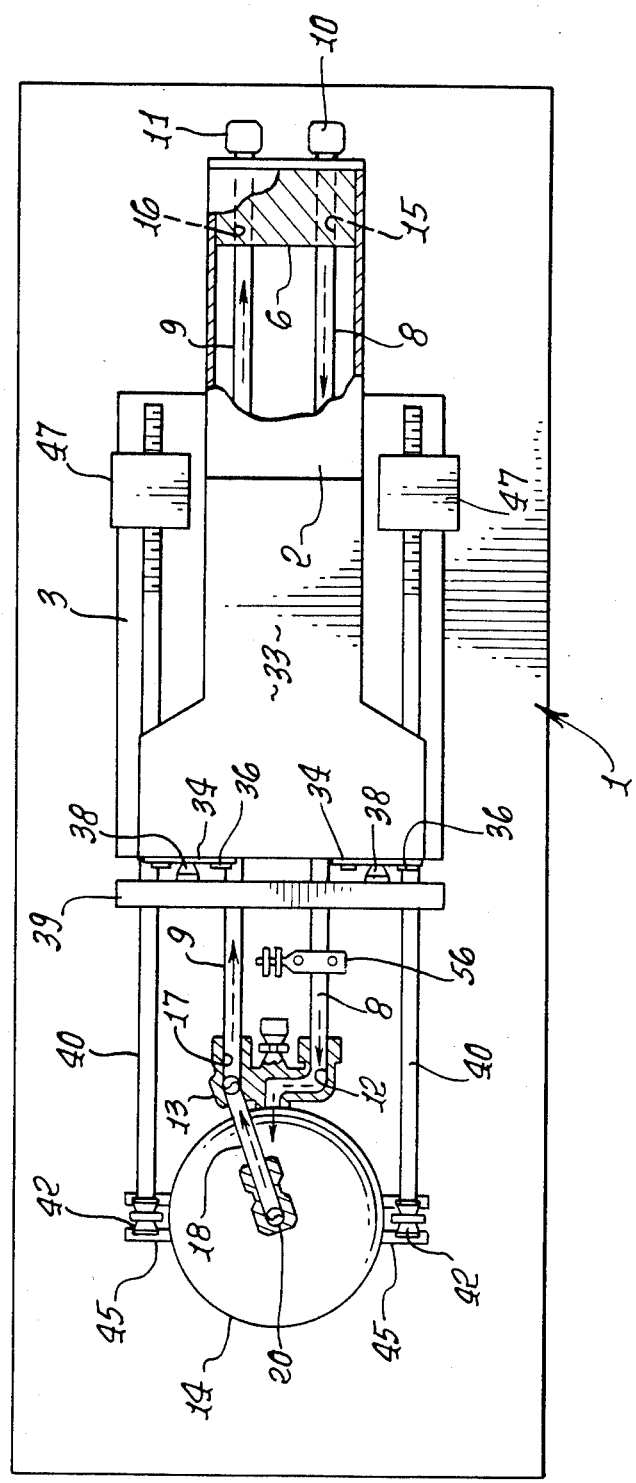
FIG. 1 is a top view of the device, showing the flow pattern of the fluid, the hollow flexures, the bulb and the counter-balance beam.

Referring now to the drawings, the improved density meter includes a platform 1 which can be mounted in a raised position by means of a pipe stand or pipe saddle. A flexure housing 2 is secured to a housing base 3 by welding or otherwise, the housing base being mounted to the platform 1 by means of four leveling screws, generally designated at 4. A block 6 is secured to the flexure housing 2 by suitable means.

Figure 3:
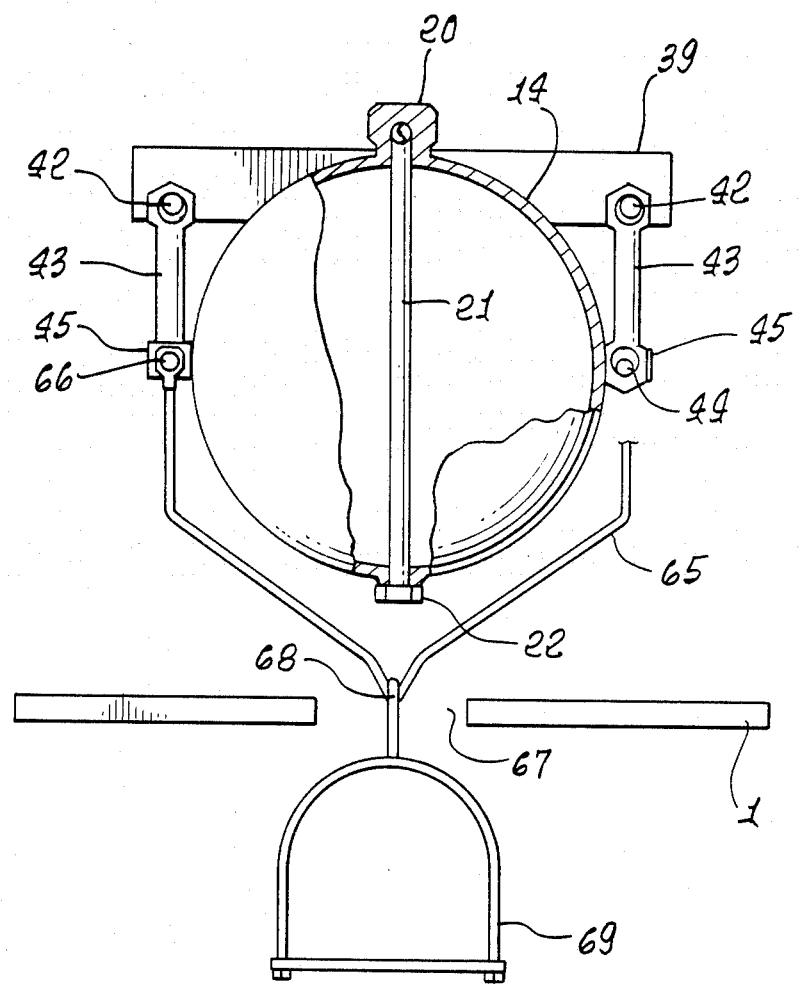
FIG. 3 is a front view, showing the internal cross-section of the bulb.

One end of each hollow flexure 8 and 9 is fastened by silver soldering or otherwise to screw-threaded connectors 10 and 11, which are receive in threaded openings of block 6, concentric with bores 15 and 16. The opposite end of the hollow flexure 8 is anchored within a bore 12 of manifold 13 by compression fitting or otherwise, the said manifold being secured to the bulb 14, so that the hollow flexure has communication with the interior of said bulb. The flexures yieldably and resiliently flex under bonding exerted by fluid in bulb 14. The opposite end of the hollow flexure 9 is anchored within a bore 17 of manifold 13 by means of compression fitting or otherwise. One end of a tube 18 is anchored to said bore 17 and the opposite end of said tube 18 is anchored in the bore of fitting 20, said fitting being secured to bulb 14. Depending from the fitting 20 and diametrically disposed within the bulb is tube 21, as seen in FIG. 3. The lower end of that tube is spaced slightly above the shank of a cap 22 so as to permit fluid ingress. In the connections as described above, the end of hollow flexure 9 has communication with the interior of bulb 14 through tube 21.

An inlet tube 24 has one end thereof anchored within the fitting 10, and the tube is also attached to the temperature transducer 26, the pressure transducer 25, and the bulkhead fitting 23 by means of compression fittings or otherwise. The bulkhead fitting 23 is secured in the bore 27 of platform 1, so that the interior of tube 24 has communication with the pressure sensor 28, the temperature sensor 29, and the interior bores of fittings 10, 23. The outlet tube 30 is anchored within the fitting 11 and the bulkhead fitting 31 by means of compression fittings or otherwise, the bulkhead fitting 31 secured in the bore 32 of platform 1, so that the interior of tube 30 has communication with the interior bores of fittings 11 and, 31.

Figure 4:
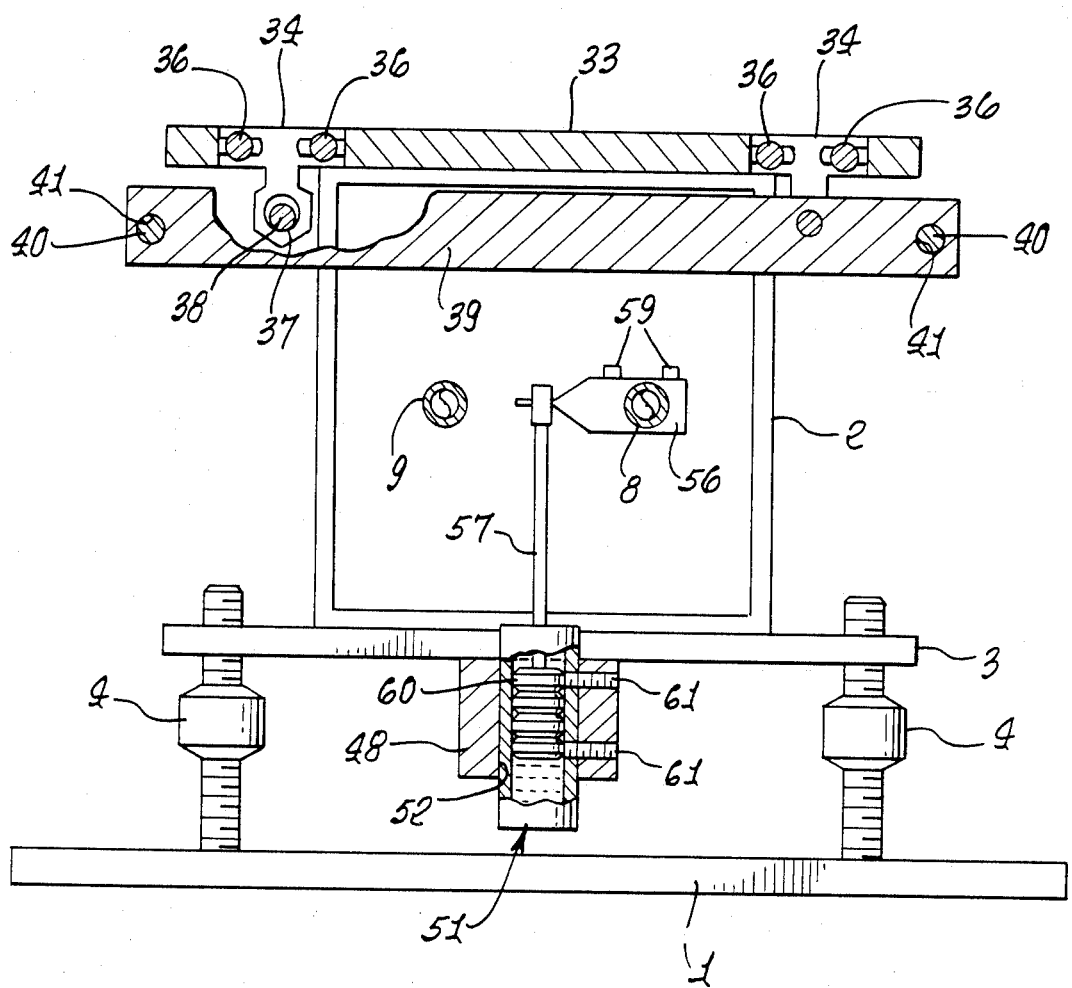
FIG. 4 is a front cross-sectional view that shows the detail of the beam support.
Figure 5:
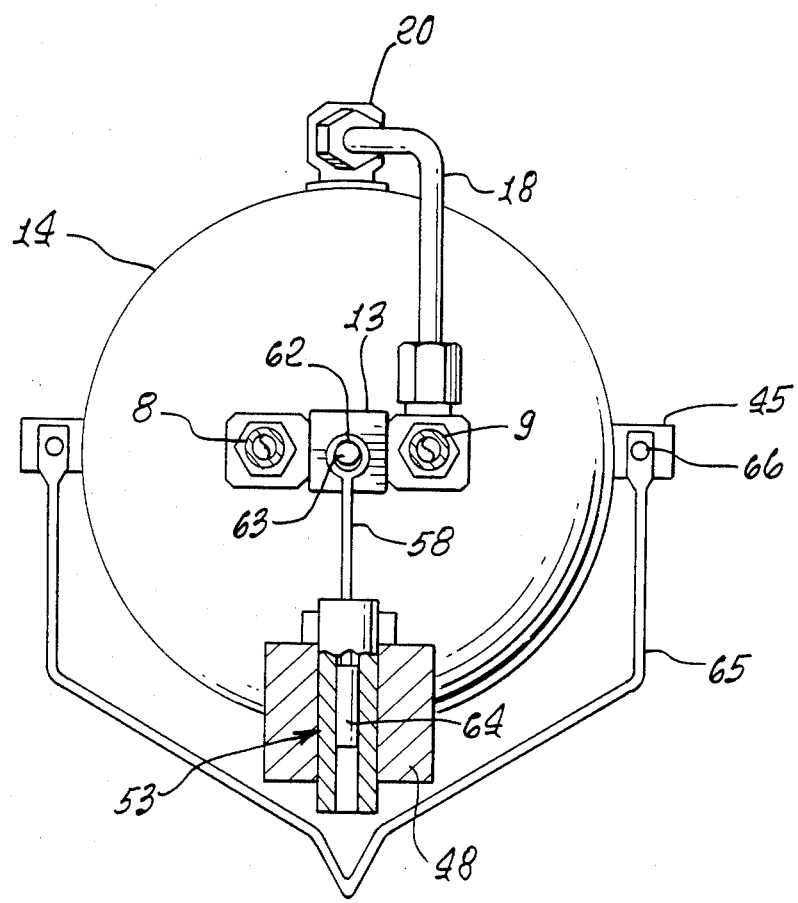
FIG. 5 is a rear view of the bulb showing details of the connections between the bulb, the flexures, and the displacement transducer.

As shown in FIG. 4, a cross plate 33 is secured to the flexure housing 2 by means of welding or otherwise, and plate 33 has secured thereto a pair of depending knife-edged members 34 as by screw means 36. The knife-edged members are adapted to support a beam cross piece 39, and a pair of bearings 38 of said crosspiece, each resting upon the respective knife edge 37 of the member 34. This provides the fulcrum of the beam.

Two beam rods 40 are anchored within a pair of bores 41 of the beam cross piece 39 by means of silver soldering or otherwise. One end of each beam rod 40 is provided with a bearing 42. A pair of double knife-edged members 43 has the knife edges thereof supported by the bearings 42 and in turn support the pair of bearings 44, such bearings being anchored to a pair of fittings 45 by screwed means. The said fittings 45 are secured to the bulb 14 by means of welding or otherwise, so that the weight of bulb is partially supported by the beams assembly 46.

The opposite ends of the pair of beam rods 40 are threaded and are received into the threaded bores of a pair of weights 47. The positions of the counter weights on the rods are adjustable. The beam assembly with weights acts as an adjustable counterbalance to partially support the weight of the bulb. This serves as a rough mechanical tare.

A support arm 48 is secured to the housing base 3 by means of a pair of threaded bolts 49 anchored through a pair of bores 50. The said bores are of a slightly larger diameter than the bolts, so that the position of the support arm 48 is adjustable.

A damper body 51 is anchored within the bore 52 of the support arm 48 by screwed means 61. A link 57, provided with a pinned adjustable slide block 56, is interposed between the hollow flexure 8 and the damper element 60 in body 51. The damper is filled with a light oil so that vibrations of the flexures 8, 9 are reduced.

A displacement transducer 53 is anchored within the bore 54 of the support arm 48 by threaded means 55. A link 58, provided with a knife edge 62 is supported by bearing 63, said bearing being secured to the bulb manifold 13. The link 58 is secured by means of solder or otherwise to the movable component 64 of the displacement transducer 53, so that any change in the position of the bulb manifold 13 will result in a change of the relative positions of the displacement transducer body and the movable component of the transducer. The fact that the support arm 48 is adjustable is critical for the proper alignment of the displacement transducer 53 and the movable component 64 thereof.

Figure 2:
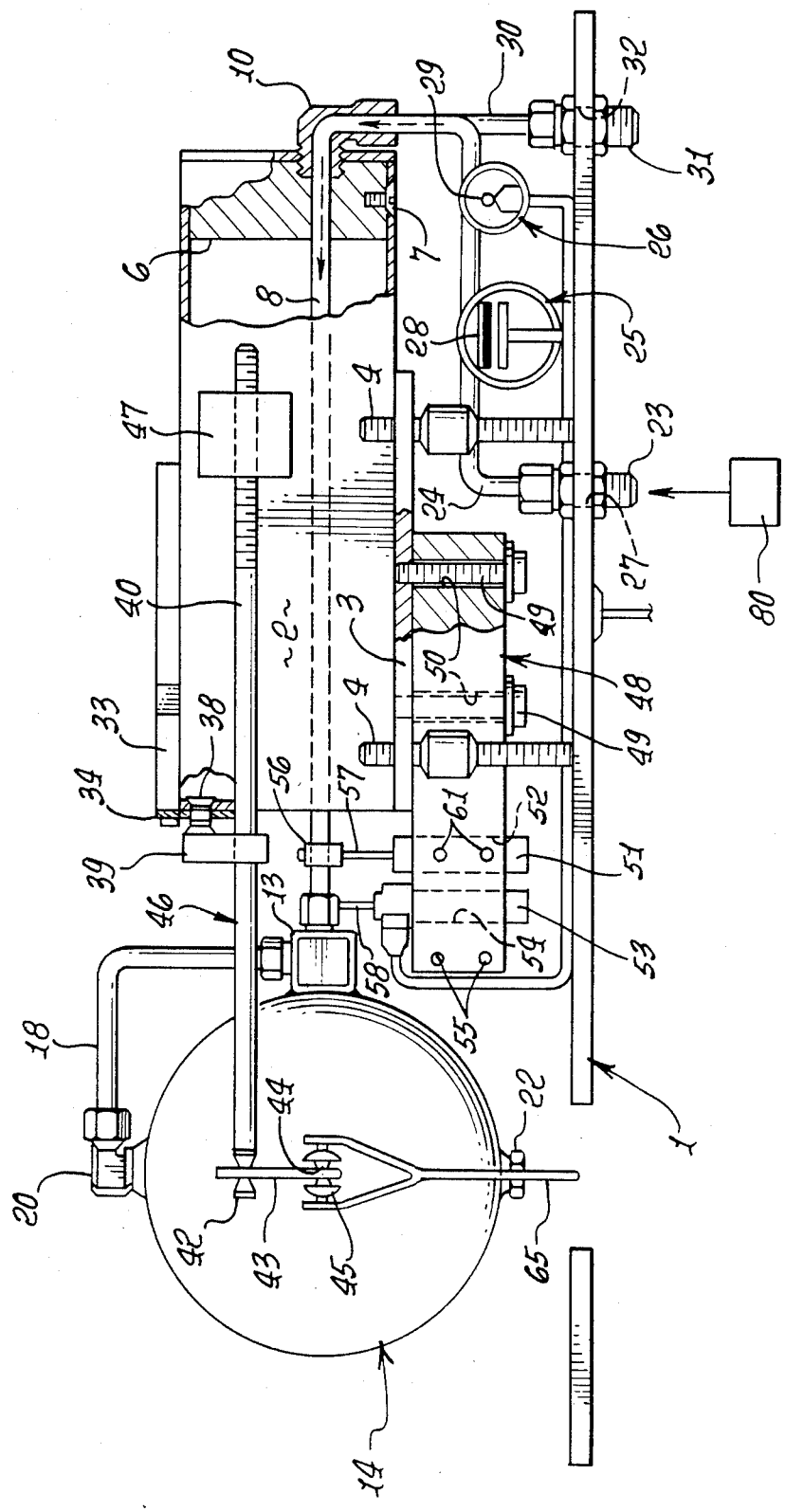
FIG. 2 is a side view of the device, plainly showing the location of the transducers and electrical connections.

As seen in FIGS. 2 and 3, a continuous curved link 65 is secured to both ends to the pair of fittings 45, by means of screws or otherwise, so that said link hangs below the bulb 14 in a position just above the large diameter bore 67 within the platform 1. The weight pan 69 is connected to the link 65 by means of the hook 68 and receives standard weights during the calibration of the density device.

Figure 6:
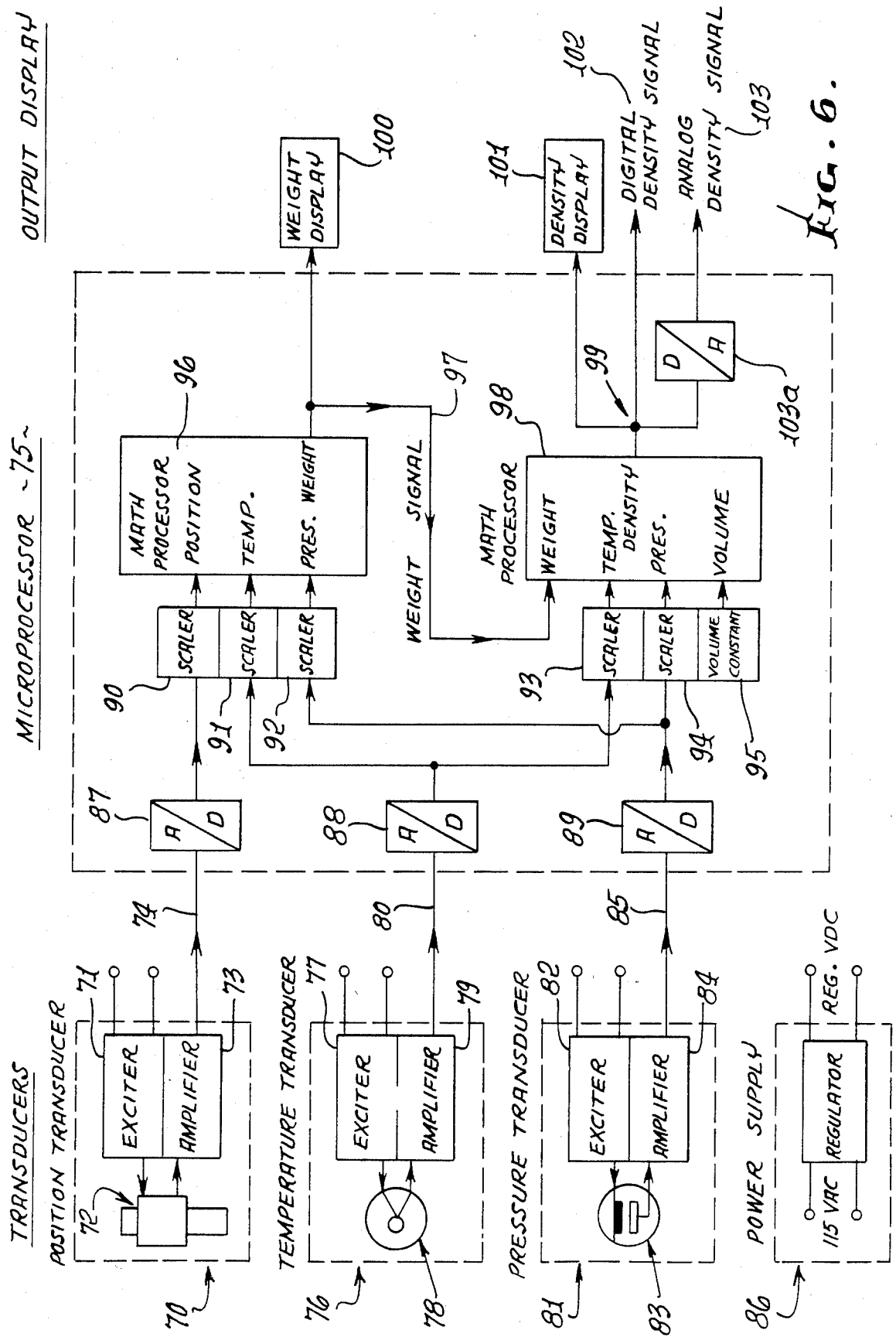
FIG. 6 is a generaly schematic view of the electric components and their relative arrangement, and also showing the general flow of information and the processing scheme.

In FIG. 6 a position transducer circuit 70 is shown to consist of a means 71 to excite the transducer, the transducer means 72 (corresponding to 53) and an amplication means 73. This circuit produces an analog position signal 74 that is converted to a digital signal by means 87, scaled by means 90, and received for mathematical processing by means 96 of the microprocessor circuit 75.

A temperature transducer circuit 76 as shown to consist of a means 77 to excite the temperature probe, the temperature probe 78 (corresponding to 26) and an amplification means 79. This circuit produces an analog temperature signal 80 that is converted to a digital signal by means 88, scaled by means 91 and 93, and received for mathematical processing by means 96 and 98 of the microprocessor circuit 75.

A pressure transducer circuit 81 is shown to consist of a means 82 to excite the transducer, the pressure transducer 83 (corresponding to 25) and an amplification means 84. This circuit produces an analog pressure signal 85 that is converted to a digital signal by means 89, scaled by means 92 and 93, and received for mathematical processing by means 96 and 98 of the microprocessor circuit 75.

A power supply circuit 86 converts the incoming 117 volt alternating current power to regulated direct current power. This power is received by the transducer circuits 70, 76, 81 and the microprocessor circuit 75.

A digital weight signal 97 is produced by the math processor 96 primarily from the position signal 74. (Additionally, said position signal 74 is corrected for changes of temperature and pressure signal 85 into the mathematical equations of the processor 96). The digital weight signal 97 is displayed by means 100 so that the device can be calibrated, and said signal is received by math processor 98.

A digital signal that represents the effective volume of the bulb 14 is produced by means 95 and received for mathematical processing by means 98 of the microprocessor circuit 75. This signal represents the volume of the bulb at the datum pressure and temperature; that is at the temperature and pressure at which the effective volume was determined during the calibration of the device. Any change in temperature or pressure will result in a change of effective volume.

A digital density signal is produced by the math processor 98 by dividing the weight signal 97 by the corrected volume value. This corrected volume value is produced in math processor 98 by combining signals from means 93, 94 and 95. The said density signal is displayed by means 101, available as a digital signal by means 102 and coverted to an analog signal 103 by means 103a.

The calibration, operation, and advantages of the continuous density meter just described are as follows:

In order to clearly understand the operation of the device it is best to describe the operation as two separate fundamental functions: the weight determining function and the volume determining function.

As a weighing device the principle of operation is based on a sum of forces; that is, the position of the bulb 14 (and therefore the output of the displacement transducer) as a function of the spring force of the flexure 8, 9; the counterbalance force of the beam 46 and weights 47; and the weight force of the fluid and blub 14 mass. The sum of these forces is always zero at any equilibrium condition.

The spring force due to displacement of the flexures 8, 9 can be either negative or positive in reference to gravity, depending on whether the displacement is up or down in reference to the neutral position (approximately level horizontally).

The counterbalance force due to the beam 46 and counterbalance weights 47 and the weight force due to the bulb 14 mass are both constants.

Thus the force due to the mass of the fluid is constantly in equilibrium with the force due to the flexures 8, 9 and the weight of the mass is proportional to the displacement of the flexures and therefore to the output signal from the displacement transducer 53.

The device is first calibrated as a weighing device whilst it is completely empty of fluid. The weight tray 69 is connected to the link 65 and all electronics are energized. A standard weight equal to approximately fifty percent of the desired range is supported on the tray 69 and the counter-balance weights 47 are in the neutral position.

With the tray 69 and weight removed from link 65 the math processor 96 is programmed to produce a zero weight signal 97. With the tray 69 and a standard weight equal to one hundred percent of range (weight of both tray 69 and standard weight together are known and equal to one hundred percent of the desired range) the math processor 96 is programmed to produce the desired weight signal 97. That is if the weight of the tray 69 and the standard weight equal 1000 grams then the weight signal 97 is programmed to display 1000 grams. During this process the weight math process 96 automatically linearizes the process.

Using constant values that have been determined experimentally, the temperature scaler 91 and the pressure scaler 92 are programmed to compensate for changes in temperature and pressure, so that the density meter is then calibrated and compensated weighing device.

The next step is to determine the effective volume and expansion coefficients for the device as assembled. The effective volume is determined because the volume (i.e. volume of bulb 14, manifold 13, and flexures 8, 9) may not have the same center of gravity as the tray 69 and weights.

Distilled water that has been deaerated is introduced into the device through fitting 23 and allowed to fill all open space within the tubes 24, 30, the flexures 8,9, the fitting 13, the bulb 14, and the transducer 25,26. The temperature and pressure of the water is varied to simulate the conditions that are expected. The values of the weight signal 97 as displayed at 100 are recorded for the various temperature-pressure combinations. The density of water at these temperature-pressure combinations can be calculated. That is, by determining the weight of a sample of fluid with a known density the effective volume of the sample can be calculated. This calculation corresponds to that described in the API "Water Calibration for Volumetric Provers" as listed above in the Background.

A volume constant 95 is derived that represents the volume of the device at 0 psig pressure and 90 degrees fahrenheit, and expansion coefficients are derived for changes in temperature and pressure. The temperature coefficient is programmed into scaler 93 and the pressure coefficient is programmed into scaler 94.

The pre-programmed math processor 98 is thereby able to calculate the effective volume of the device at any combination of temperature and pressure, although no separate volume signal is displayed. Typically, the math processor 98 is continually dividing the weight signal 97 by a volume algorithm and provides a density signal 99 for display 101, direct digital 102 use by another microprocessor, and conversion to an analog signal 103.

A major advantage of the device is that it is calibrated using standard weights and standard weight methods. THe data for the density of water is well established and readily accessible. The weight calibration can be checked easily in the field without even removing the case, with access through the bore 67 in the platform. The volume calibration is not prone to change except by buildup of waxes on the inner walls when densities of hydrocarbon fluids are determined. This problem is observed as a consistent shift in the zero position and is remedied by cleaning with solvent.

In the operation of the density meter, a means to continuously carry fluid to the flexure 8 is shown at 80. The unknown fluid flows through the device as described above, as the density of the fluid changes, the weight signal 97 changes; and as the temperature and pressure change, the volume changes. Thus the density signal 99 is constantly being updated and compensated.

I claim:
1. In a density device, the combination comprises:
   (a) a plurality of hollow flexures,
   (b) a relatively fixed support for one end of each of said flexures,
   (c) and a closed container supported by, and interiorly communicating with the opposite ends of said flexures; one or more of said flexures serving to conduct a flowing fluid into the container and the other of said flexures serving to conduct a flowing fluid out of the container; changes in fluid density producing flexure deflection and said container when filled with fluid being supported in every position by said deflecting flexures;

(d) a first means to convert said deflection into an electrical displacement signal, (e) a second means connected to said first means to convert said electrical displacement signal to an electrical weight signal, (f) a third means to produce an electrical volume signal, (g) a fourth means connected to said second means and to said third means to combine said weight signal with said volume signal to produce a density signal, (h) and including a pressure sensing device to convert the pressure of the flowing fluid into an electrical pressure signal, and a temperature sensing device to convert the temperature of the fluid into an electrical temperature signal, and wherein said second means is connected to said first means and to said temperature sensing device for converting said displacement signal and said temperature signal into a temperature compensated weight signal; and wherein said fourth means is connected to said second means, third means, pressure sensing device and temperature device and combines said temperature compensated weight signal, said volume signal, said temperature signal and said pressure signal to produce a temperature and pressure compensated density signal.

2. The combination of claim 1 wherein said flexures comprise generally horizontally and parallel extending metallic tubes fixedly supported in spaced relation to yieldably flex under loading exerted by fluid in the container.

3. The combination of claim 1 including means operatively connected to the container to support calibrating weights.

4. The combination of claim 1 wherein the tubular flexures have ends respectively located at the side of the container, which is generally spherical, one flexure communicating with the interior of the container via that side, and the other flexure communicating with the upper interior of the container via a tubular line that extends to the top of the container.

5. The combination of claim 1 wherein said first means includes a transducer connected to one of the flexures near its end proximate the container.

6. The combination of claim 1 including damping means connected with said resiliently yieldable flexures to damp their flexing.

7. In a density device, the combination comprising:

(a) a plurality of hollow flexures, (b) a relatively fixed support for one end of each of said flexures, (c) and a closed container secured to, partially supported by, and interiorly communicating with the opposite ends of said flexures; one or more of said flexures serving to conduct a flowing fluid into the container and the other of said fleuxres serving to conduct a flowing fluid out of the container, (d) a counterbalance beam cooperating with said flexures for supporting the container, adjustable means for balancing said beam, said container and its fluid contents in every position of the flexure, whereby changes in density of fluid in the container and flexure produce deflection of said flexure, (e) a first means to convert said deflection into an electrical displacement signal, (f) a second means connected to said first means to convert said electrical displacement signal to an electrical weight signal, (g) a third means to produce an electrical volume signal, (h) a fourth means connected to said second means to said third means that combines said weight signal with said volume signal to produce a density signal, and means to continuously convey incoming fluid to one of the flexures, (i) and also including a pressure sensing device to convert the pressure of the flowing fluid into an electrical pressure signal, and a temperature sensing device to convert the temperature of the fluid into an electrical temperature signal, and wherein said second means is connected to said first means and to said temperature sensing device for converting said displacement signal and said temperature signal into a temperature compensated weight signal, and wherein said fourth means is connected to said second means, third means, pressure sensing device and temperature sensing device and combines said temperature compensated weight signal, said volume signal, said temperature signal and said pressure signal to produce a temperature and pressure compensated density signal.

* * * * *